United States Patent [19]

Hansen

[11] Patent Number: 4,639,453

[45] Date of Patent: Jan. 27, 1987

[54] SUBSTITUTED 1-(4-AMINO-6,7-DIALKOXYQUINAZOLINYL)-4 CYCLOHEXENYL DERIVATIVES OF PIPERAZINE AND HOMOPIPERAZINE, PROCESSES FOR THEIR PREPARATION AND THEIR USE, FORMULATIONS CONTAINING THESE COMPOUNDS AND INTERMEDIATES

[75] Inventor: Werner Hansen, Hamburg, Fed. Rep. of Germany

[73] Assignee: Beiersdorf Aktiengesellschaft, Hamburg, Fed. Rep. of Germany

[21] Appl. No.: 679,178

[22] Filed: Dec. 7, 1984

[30] Foreign Application Priority Data

Dec. 23, 1983 [DE] Fed. Rep. of Germany ....... 3346675

[51] Int. Cl.$^4$ ................. A61K 31/505; C07D 403/04; C07D 405/14
[52] U.S. Cl. .................... 514/254; 544/230; 544/291; 544/399; 540/575
[58] Field of Search ............... 544/291, 230; 260/243.3; 514/254

[56] References Cited

U.S. PATENT DOCUMENTS 3,594,480  7/1981  Cronin et al. ............ 514/254
3,635,979  1/1972  Hess .................... 544/291
4,377,581  3/1983  Hess et al. ............. 544/291

Primary Examiner—Glennon H. Hollrah
Assistant Examiner—James H. Turnipseed
Attorney, Agent, or Firm—Sprung Horn Kramer & Woods

[57] ABSTRACT

New substituted 1-(4-amino-6,7-dialkoxyquinazolinyl)-4-cyclohexenyl derivatives of piperazine and homopiperazine, of the general formula I

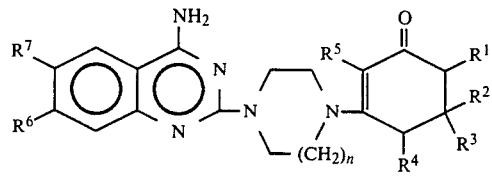

in which $R^1$, $R^2$, $R^3$, $R^4$ and $R^5$, which can be identical or different, denote hydrogen, straight-chain or branched alkyl groups with in each case 1 to 6 carbon atoms, cyclic aliphatic radicals with in each case 5 to 7 carbon atoms, aromatic radicals or substituted aromatic radicals, which can be monosubstituted or polysubstituted by identical or different substituents from the group comprising halogen and lower alkyl groups with in each case 1 to 4 carbon atoms in the alkyl part, or denote aralkyl radicals, furanyl radicals or thienyl radicals, or $R^2$ and $R^3$ together denote the group $-(CH_2)_a-$, wherein a is the number 4 or 5, or $R^3$ and $R^4$ together denote the group $-(CH_2)_b-$, wherein b is the number 3, 4 or 5, $R^6$ and $R^7$, which can be identical or different, denote alkoxy groups with 1 to 4 carbon atoms in the alkyl part, which can be straight-chain or branched, and n denotes the number 1 or 2, and tautomeric forms thereof, as well as acid addition salts and hydrates thereof, reduce the arterial blood pressure and promote blood flow in the vessels. They can be used as medicaments for the treatment of hypertension, glaucoma and cardiac insufficiency.

10 Claims, No Drawings

SUBSTITUTED 1-(4-AMINO-6,7-DIALKOXYQUINAZOLINYL)-4 CYCLOHEXENYL DERIVATIVES OF PIPERAZINE AND HOMOPIPERAZINE, PROCESSES FOR THEIR PREPARATION AND THEIR USE, FORMULATIONS CONTAINING THESE COMPOUNDS AND INTERMEDIATES

The invention relates to new substituted 1-(4-amino-6,7-dialkoxyquinazolinyl)-4-cyclohexenyl derivatives of piperazine and homopiperazine, of the general formula I

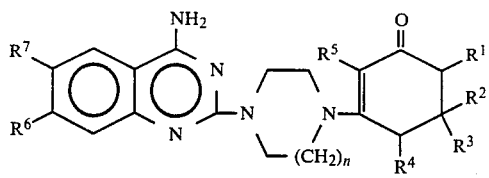

in which
$R^1$, $R^2$, $R^3$, $R^4$ and $R^5$, which can be identical or different, denote hydrogen, straight-chain or branched alkyl groups with in each case 1 to 6 carbon atoms, cyclic aliphatic radicals with in each case 5 to 7 carbon atoms, aromatic radicals or substituted aromatic radicals, which can be monosubstituted or polysubstituted by identical or different substituents from the group comprising halogen and lower alkyl and alkoxy groups with in each case 1 to 4 carbon atoms in the alkyl part, or denote aralkyl radicals, furanyl radicals or thienyl radicals, or $R^2$ and $R^3$ together denote the group $-(CH_2)_a-$, wherein a is the number 4 or 5, or $R^3$ and $R^4$ together denote the group $-(CH_2)_b-$, wherein b is the number 3, 4 or 5, $R^6$ and $R^7$, which can be identical or different, denote alkoxy groups with 1 to 4 carbon atoms in the alkyl part, which can be straight-chain or branched, and n denotes the number 1 or 2, and tautomeric forms thereof, as well as acid addition salts and hydrates thereof, processes for their preparation and their use in pharmaceutical compositions.

The invention furthermore relates to new substituted cyclohexene derivatives of piperazine and homopiperazine, of the general formula III

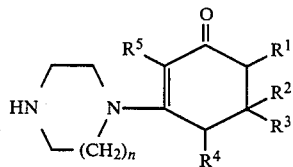

in which
$R^1$, $R^2$, $R^3$, $R^4$ and $R^5$, which can be identical or different, denote hydrogen, straight-chain or branched alkyl groups with in each case 1 to 6 carbon atoms, cyclic aliphatic radicals with in each case 5 to carbon atoms, aromatic radicals or substituted aromatic radicals, which can be monosubstituted or polysubstituted by identical or different substituents from the group comprising halogen and lower alkyl and alkoxy groups with in each case 1 to 4 carbon atoms in the alkyl part, or denote aralkyl radicals, furanyl radicals or thienyl radicals, or $R^2$ and $R^3$ together denote the group $-(CH_2)_a-$, wherein a is the number 4 or 5, or $R^3$ and $R^4$ together denote the group $-(CH_2)_b-$, wherein b is the number 3, 4 or 5, and n denotes the number 1 or 2, and tautomeric forms thereof, and acid addition salts and hydrates thereof, processes for their preparation and their use as intermediates for the preparation of the compounds of the general formula I according to the invention.

For simplicity, the compounds according to the invention are defined in only one of the tautomeric forms represented by the formulae I and III. However, the invention extends to all the tautomeric forms of the compounds. For example, compounds of the formulae I and III can also occur in other tautomeric forms if the radical $R^1$ denotes hydrogen.

Although pharmaceutically acceptable salts of the new compounds of the formula I and the tautomeric forms and hydrates thereof are preferred, all the acid addition salts lie within the scope of the invention. All the acid addition salts of the formulae I and III are useful for the preparation of the bases, even if a particular salt is only desired as an intermediate, such as, for example, if the salt is formed only for the purpose of purification or identification, or if it is used as an intermediate in the preparation of a pharmaceutically acceptable salt, for example by ion exchange procedures.

The compounds according to the invention can contain asymmetric carbon atoms. This invention thus also relates to the various optical isomers and the diastereoisomers, as well as to the hydrates and addition salts of these compounds with acids. Racemates can be resolved into their optical antipodes by methods which are known per se, for example by using optically active acids, such as tartaric acid, camphorsulphonic acid or dibenzoyltartaric acid, or as esters or ethers with optically active components or via urea inclusion compounds.

Preferred radicals $R^1$ to $R^5$ are alkyl groups, preferably methyl, ethyl, n-propyl and isopropyl groups, and cyclohexyl, phenyl and naphthyl groups. Substituted aromatic radicals, in particular phenyl groups, preferably have one or two identical or different substituents from those mentioned, and in particular fluorine, chlorine, bromine, methyl, ethyl, methoxy and ethoxy.

Arylalkyl radicals (aralkyl) are preferably those with 1 to 4, in particular 1 or 2, carbon atoms in the alkyl part, and aryl is particularly preferably phenyl. A preferred phenylalkyl radical is the benzyl group.

If $R^2$ and $R^3$ together denote the group $-(CH_2)_a-$, spiro-cyclopentane and spiro-cyclohexane compounds are obtained. The spiro-cyclohexane compounds are preferred.

If $R^3$ and $R^4$ together denote the group $-(CH_2)_b-$, b is preferably the number 4.

The radicals $R^6$ and $R^7$ are preferably methoxy and ethoxy. The 6,7-dimethoxy compounds are especially preferred.

Compounds of the formulae I and III which are furthermore preferred are those in which n is 1 or 2 and are monosubstituted or disubstituted by $R^2$ and $R^3$ in the 5-position of the cyclohexenonyl ring, $R^2$ and/or $R^3$ preferably denoting alkyl, preferably methyl, ethyl, n-propyl or isopropyl, especially dimethyl, or $R^2$ and $R^3$ together denoting the group —$(CH_2)_a$—.

Compounds of the general formula I with a therapeutic effect are listed below, in addition to the compounds mentioned in the examples: 1-(4-amino-6,7-dimethoxyquinazolin-2-yl)-4-(3-oxo-5-methyl-5-ethyl-1-cyclohexen-1-yl)-piperazine, 1-(4-amino-6,7-dimethoxyquinazolin-2-yl)-4-(3-oxo-5,5-diethyl-1-cyclohexen-1-yl)-piperazine, 1-(4-amino-6,7-dimethoxyquinazolin-2-yl)-4-(3-oxo-5-methyl-5-(n-propyl)-1-cyclohexen-1-yl)-piperazine, 1-(4-amino-6,7-dimethoxyquinazolin-2-yl)-4-(3-oxo-5-methyl-5-isopropyl-1-cyclohexen-1-yl)-piperazine, 1-(4-amino-6,7-dimethoxyquinazolin-2-yl)-4-(3-oxo-5,5-diisopropyl-1-cyclohexen-1-yl)-piperazine, 1-(4-amino-6,7-dimethoxyquinazolin-2-yl)-4-(3-oxo-5-ethyl-1-cyclohexen-1-yl)-piperazine, 1-(4-amino-6,7-dimethoxyquinazolin-2-yl)-4-(3-oxo-5-ethyl-6-ethyl-1-cyclohexen-1-yl)-piperazine, 1-(4-amino-6,7-dimethoxquinazolin-2-yl)-4-(3-oxo-5-isopropyl-6-methyl-1-cyclohexen-1-yl)-piperazine, 1-(4-amino-6,7-dimethoxyquinazolin-2-yl)-4-(3-oxo-5-isopropyl-6-ethyl-1-cyclohexen-1-yl)-piperazine, 1(4-amino-6,7-dimethoxyquinazonlin-2-yl)- 4-(3-oxo-5-isopropyl-6-isopropyl-1-cyclohexen-1-yl)piperazine and 1-(4-amino-6,7-dimethoxyquinazolin-2-yl)-4-(3-oxo-6-ethyl-1-cyclohexen-1-yl)-piperazine.

The following compounds of the general formula I and salts and hydrates thereof with a high therapeutic effect are particularly preferred, and in particular in the form of the racemates and in the form of optically active isomers and diastereoisomers: 1-(4-amino-6,7-dimethoxyquinazolin-2-yl)-4-(3-oxo-5,5-dimethyl-1-cyclohexen-1-yl)piperazine, 1-(4-amino-6,7-dimethoxyquinazolin-2-yl)-4-(3-oxo-5-methyl-1-cyclohexen-1-yl)-piperazine, 1-(4-amino-6,7-dimethoxyquinazolin-2-yl)-4-(3-oxo-5-isopropyl-1-cyclohexen-1-yl)-piperazine, 1-(4-amino-6,7-dimethoxyquinazolin-2-yl)-4-(3-oxo-5-phenyl-6-methyl-1-cyclohexen-1-yl)-piperazine, 1-(4-amino-6,7-dimethoxyquinazolin-2-yl)-4-(3-oxo-5,5-dimethyl-6-methyl-1-cyclohexen-1-yl)-piperazine, 1-(4-amino-6,7-dimethoxyquinazolin-2-yl)-4-(3-oxo-5,5-dimethyl-1-cyclohexen-1-yl)-(1,4-diaza-cycloheptane), 1-(4-amino-6,7-dimethoxyquinazolin-2-yl)-4-(3-oxo-5-methyl-6-methyl-1-cyclohexen-1-yl)-piperazine and 1-(4-amino-6,7-dimethoxyquinazolin-2-yl)-4-(3-oxo-5-thien-2-yl-1-cyclohexen-1-yl)-piperazine.

The compounds of the formula I according to the invention and their acid addition salts have useful pharmacological properties. They are suitable for reducing the arterial blood pressure and for promoting blood flow in peripheral vessels and also coronary vessels. They have proved to be effective regulators of the cardiovascular system and can be used, in particular, for the treatment of hypertension. They are furthermore suitable for the treatment of cardiac insufficiency and for reducing the intra-ocular pressure. Their relatively long period of action and their high selectivity for the alpha-1-receptors are striking.

Compared with structurally similar compounds, the compounds of the formula I according to the invention have these outstanding properties in a manner which cannot be predicted.

In particular, they are distinguished by a long-lasting antihypertensive effect on rats, rabbits and cats. Extremely low doses of 1 to 100 μg/kg of body weight are required for this.

In humans, 0.01 to 50 mg/day, in particular 0.1 to 5 mg/day, are suitable for reducing the arterial blood pressure. This dosage is also suitable for the treatment of cardiac insufficiency.

As a result of their highly selective alpha-sympatholytic properties, the compounds according to the invention and addition salts thereof can furthermore be used for reducing increased intra-ocular pressure (glaucoma). The dosages at the preferred concentration of 0.1 to 10 mg/ml, corresponding to a 0.01 to 1% strength aqueous solution, are preferably several drops per eye twice to three times daily.

The invention provides pharmaceutical compositions containing a compound of the formula I or pharmaceutically acceptable salts thereof, together with a pharmaceutically acceptable diluent or excipient.

The compounds according to the invention can be mixed with the usual pharmaceutically acceptable diluents or excipients and, if appropriate, with other auxiliaries and can be administered, for example, orally or parenterally. They can be administered orally in the form of tablets, coated tablets, syrups, suspensions and liquids, or parenterally in the form of solutions or suspensions. Products to be administered orally can contain one or more additives, such as sweeteners, aromatising agents, colorants and preservatives. Tablets can contain the active compound mixed with the customary pharmaceutically acceptable auxiliaries, for example inert diluents, such as calcium carbonate, sodium carbonate, lactose and talc, granulating agents and agents which promote the disintegration of the tablets on oral administration, such as starch or alginic acid, binders, such as starch or gelatine, and lubricants, such as magnesium stearate, stearic acid and talc.

Examples of suitable excipients are milk sugar (lactose), gelatine, maize starch, stearic acid, ethanol propylene glycol, ethers of tetrahydrofuryl alcohol and water.

The tablets can be coated by known procedures in order to delay disintegration and absorption in the gastrointestinal tract, by which means the activity of the active compound can extend over a longer period of time. The active compound can also be mixed in the suspensions with auxiliaries which are usual for the preparation of such compositions, for example suspending agents, such as methylcellulose, tragacanth or sodium alginate, wetting agents, such as lecithin, polyethylene stearate and polyoxyethylene sorbitan monooleate, and preservatives, such as ethyl parahydroxybenzoate. Capsules can contain the active compound as the sole constituent or mixed with a solid diluent, such as calcium carbonate, calcium phosphate or kaolin. The injectable products are likewise formulated in a manner which is known per se. The pharmaceutical products can contain the active compound in an amount of 0.1 to 90%, in particular 1 to 90%, the remainder being an excipient or additive. In view of the preparation and administration, solid products, such as tablets and capsules, are preferred. The products preferably contain the active compound in an amount of 0.1 to 50 mg.

The new compounds of the general formula I can be obtained by the following processes:

The first process for the preparation of the compounds of the general formula I is characterised in that quinazoline derivatives of the general formula II

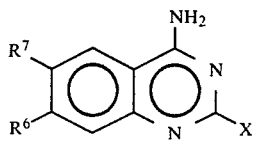

(II)

in which X is halogen, preferably chlorine or bromine, or alkylmercapto, preferably methylmercapto, and $R^6$ and $R^7$ have the abovementioned meaning, are reacted with cyclohexenone derivatives of piperazine or homopiperazine, of the general formula III.

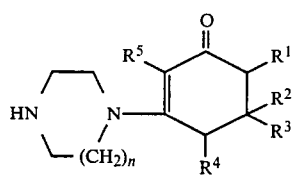

(III)

in which $R^1$ to $R^5$ and n have the abovementioned meaning.

The reaction is carried out in suitable solvents or dispersing agents, such as toluene, xylene, halogenated hydrocarbons, preferably chlorobenzene, or alcohols, preferably isoamyl alcohol. The reaction is carried out at the boiling point of the solvent, preferably at a temperature of 80°–150° C. The molar ratio of reactants II and III is 1:1. An excess of 10% of the compound III is preferably taken. The reaction can also be carried out with acid-binding agents, such as potassium carbonate or triethylamine.

The preparation of the starting compounds of the formula II is known or can be carried out by processes analogous to those known from the literature (for example J. Chem. Soc., London, 1948, page 1764; U.S. patent specification No. 3,511,836; and J. med. Chem. 20, 148 (1977)). Compounds where X=S-alkyl in formula II are likewise known (German Offenlegungsschrift No. 1,620,138). The intermediates of the formula III are new.

In a second process for the preparation of the compounds of the general formula I, quinazoline derivatives of the general formula II where X, $R^6$ and $R^7$ have the abovementioned meaning are used as starting substances and are reacted with piperazine or homopiperazine (1,4-diaza-cycloheptane) of the general formula IV in a known manner (analogous to German Offenlegungsschrift No. 1,620,138 and U.S. patent specification No. 4,001,237). The compounds of the formula IV are masked with a protective group Q, for example with an acyl group, preferably the easily detachable formyl group or a carbalkoxy group. The protective group can be detached by acid hydrolysis, in the first case, and advantageously first by alkaline hydrolysis and then by acid hydrolysis, in the second case, from the reaction product of the formula V initially obtained, to give the reaction product of the formula VI.

As a protective group against reaction of the second imino group of the piperazine or homopiperazine, it is also possible to use, for example, hydrobromic acid in a ratio to the amine of 1:1, so that the piperazine or homopiperazine is in the form of the monohydrobromide:

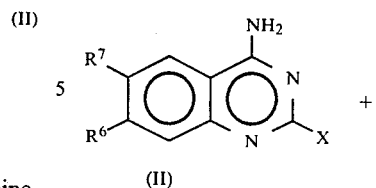

(II)

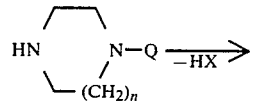

(IV)

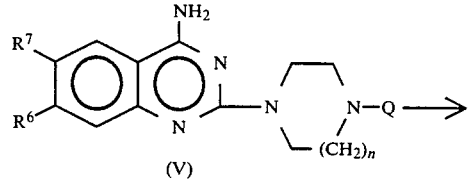

(V)

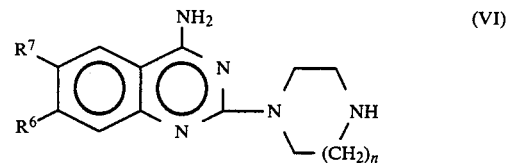

(VI)

The second process for the preparation of the compounds of the general formula I according to claim 1 is characterised in that compounds of the general formula VI

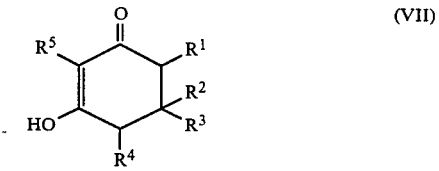

(VI)

in which $R^6$, $R^7$ and n have the abovementioned meaning, are reacted with 1,3-dioxocyclohexanes of the general formula VII

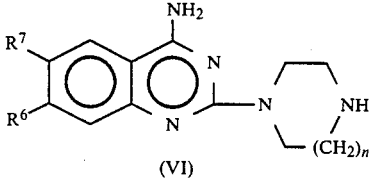

(VII)

in which $R^1$ to $R^5$ have the abovementioned meaning.

The condensation is carried out in a solvent at elevated temperature, preferably in boiling toluene.

The 1,3-dioxocyclohexanes of the formula VII and the tautomeric forms thereof are known or can be obtained by know processesss. They are preferably prepared in accordance with one of the following two equations (R=lower alkyl):

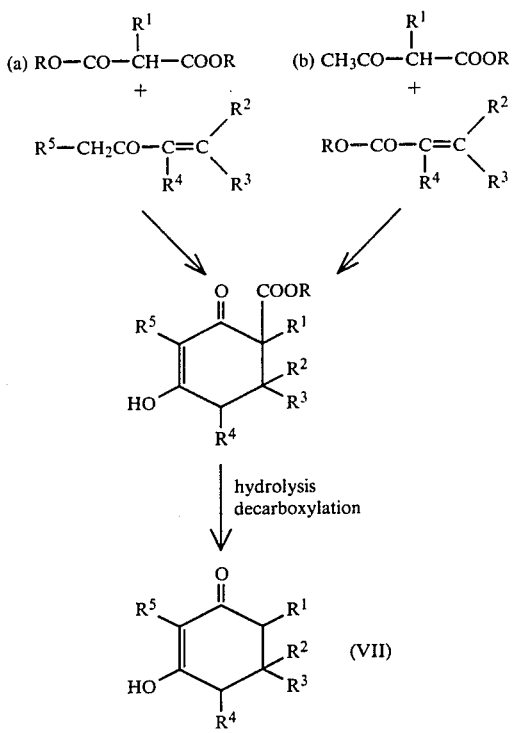

In process (a), monosubstituted or unsubstituted malonic esters are reacted with unsaturated ketones, which can be obtained by condensation of two ketones or a ketone and an aldehyde under alkaline or acid conditions (aldol condensation).

In process (b), monosubstituted or unsubstituted β-keto acid esters are reacted with substituted acrylic acid esters.

After hydrolysis and decarboxylation of the reaction products initially formed, the compounds according to formula VII are obtained.

The starting compounds used in the process are known or can be prepared by known methods.

In some cases, especially for the preparation of the compounds according to the invention substituted by $R^4$, the 1,3-dioxo-cyclohexane derivatives of the formula VII or IX can also be prepared by hydrogenation of resorcinol derivatives VIII in the presence of a catalyst, preferably Raney nickel:

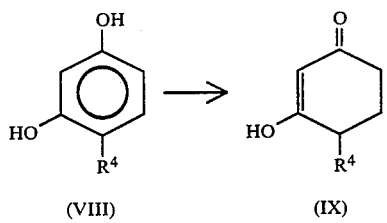

The intermediates of the general formula III according to the invention are not described in the literature. The process for the preparation of the compounds of the general formula III with the abovementioned meaning of the radicals $R^1$ to $R^5$ and n is characterised in that piperazine or homopiperazine is subjected to a condensation reaction with compounds of the general formula VII with the abovementioned meaning of the radicals $R^1$ to $R^5$. The reaction is carried out in a solvent at elevated temperature, preferably in boiling toluene.

The compounds of the general formula I can be isolated from the reaction mixtures either as bases or in the form of their salts. As bases, they can be converted into salts with suitable inorganic or organic acids by known processes.

Physiologically acceptable salts are preferred. Examples of inorganic acids which are suitable for this are the hydrogen halide acids, for example hydrochloric acid, and sulphuric acid, and examples of suitable organic acids are fumaric acid, maleic acid, citric acid and tartaric acid. For the preparation, an alcoholic solution of a suitable acid is added to a solution of the base and, after addition of ether, the salt is obtained.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Diastereomers can be separated into their racemic modifications in a known manner on the basis of the physicochemical differences of the constituents, for example by chromatography and/or fractional crystallisation.

Racemates can be resolved according to known methods, for example by recrystallisation from an optically active solvent, with the aid of micro-organisms or by reaction with an optically active acid which forms salts with the racemic compound, and separation of the diastereoisomers by fractional crystallisation, from which the enantiomers can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Advantageously, the more active of the two antipodes is isolated. According to the invention it is however also possible to obtain the pure enantiomers by asymmetric synthesis.

The following examples serve to illustrate the invention:

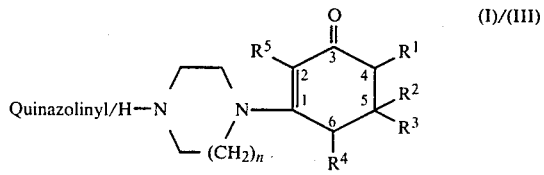

EXAMPLE 1

(3-Oxo-5,5-dimethyl-1-cyclohexen-1-yl)-piperazine

A mixture of 28.0 g (0.2 mol) of 1,3-dioxo-5,5-dimethyl-cyclohexane (dimedone), 51.7 g (0.6 mol) of anhydrous piperazine and 250 ml of toluene is heated at the boiling point under reflux for 3 hours, using a water separator. The toluene and most of the excess piperazine are then distilled off in vacuo at a bath temperature of 60° C. The residue which remains is dissolved in 300 ml of chloroform. To remove the piperazine and dimedone, the chlorform solution is shaken three times with 50 ml of water each time. After the chloroform solution has been dried with sodium sulphate, it is concentrated. The residue solidifies and has a melting point of 112°–15° C. (yield: 25.2 g=60%, yellow crystals). A sample of (3-oxo-5,5-dimethyl-1-cyclohexen-1-yl)-piperazine recrystallised from toluene/cyclohexane (1:2 (by volume)) has a melting point of 115°–116° C.

$R_F$ value: 0.39

Eluant: methyl alcohol/ethyl acetate/diethylamine=50:45:5 (by volume)

Thin layer chromatography pre-coated plate: silica gel 60 $F_{254}$ with a concentration zone, MERCK No. 11846.

EXAMPLE 2

(3-Oxo-5,5-dimethyl-1-cyclohexen-1-yl)-homopiperazine

A mixture of 9.8 g (0.07 mol) of dimedone, 21.0 g (0.21 mol) of anhydrous 1,4-diaza-cycloheptane (homopiperazine) and 150 ml of toluene is heated at the boiling point under reflux for 3 hours, using a water separator. After the toluene and excess homopiperazine have been removed (bath: 60° C., vacuum), the residue which remains is dissolved in 20 ml of chloroform and purified by chromatography by means of a 400 g silica gel S column (elution with chloroform containing an increasing proportion of methanol (1–10%)). The resulting purified fractions are combined and concentrated. An oil of (3-oxo-5,5-dimethyl-1-cyclohexen-1-yl)-homopiperazine remains in an amount of 11.4 g (=73% yield).

To prepare the hydrochloride, this amount is dissolved in 50 ml of absolute ethyl alcohol, and hydrogen chloride, dissolved in ethyl alcohol, is added. After addition of anhydrous ether, the dihydrochloride monohydrate precipitates. When washed with anhydrous ether, 10.7 g (=49% yield) of the hydrochloride of (3-oxo-5,5-dimethyl-1-cyclohexen-1-yl)-homopiperazine of melting point 208°–212° C. are obtained.

$R_F$ value: 0.39 (conditions corresponding to Example 1)

EXAMPLE 3

[3-Oxo-5-(o-chlorophenyl)-1-cyclohexen-1-yl]-piperazine

A mixture of 24.0 g (0.108 mol) of 1,3-dioxo-5-(o-chlorophenyl)-cyclohexane, 28.4 g (0.33 mol) of anhydrous piperazine and 270 ml of toluene is heated at the boiling point under reflux for 5 hours, using a water separator. The toluene is distilled off, while still warm, in vacuo and the residue is dissolved in chloroform. This solution is extracted three times by shaking with water, to remove the excess piperazine, and dried with sodium sulphate. The concentrated solution is purified by means of column chromatography (corresponding to Example 2). Some of the fractions contain 6.5 g of the base [3-oxo-5-(o-chlorophenyl)-1-cyclohexen-1-yl]-piperazine in pure form, of melting point 159°–160° C., and another portion is still contaminated. The latter is purified by the oxalate: 6.2 g of a white salt of melting point 225°–227° C. (decomposition). After converting back into the base, a further 5.0 g are obtained. Total yield: 11.5 g (=36.7%). $R_F$ value: 0.38 (conditions corresponding to Example 1).

EXAMPLE 4

(3-Oxo-6-cyclohexyl-1-cyclohexen-1-yl)-piperazine

A mixture of 9.8 g (0.05 mol) of 1,3-dioxo-6-cyclohexyl-cyclohexane, 12.9 g (0.15 mol) of anhydrous piperazine and 150 ml of toluene is reacted and worked up as described in Example 1. For purification, column chromatography is included (corresponding to Example 2). (3-Oxo-6-cyclohexyl-1-cyclohexen-1-yl)-piperazine is obtained as an oil in an amount of 9.9 g (=76% yield) with an $R_F$ value of 0.36 (conditions corresponding to Example 1). The dihydrochloride has a melting point of 258°–261° C. (decomposition).

The 1,3-dioxo-6-cyclohexyl-cyclohexane used above is prepared from a known resorcinol derivative in accordance with a specification (Friedländers Fortschritte der Teerfarbenfabrikation 22, 618, Verlag Julius Springer, Berlin and German Patent Specification No. 621,915), as follows:

20.0 g (0.104 mol) of 4-cyclohexylresorcinol are dissolved in 40 ml of ten percent strength sodium hydroxide solution and are hydrogenated in the presence of 5 g of Raney nickel in an autoclave at 90° under 20 bar for 5 hours. The reaction mixture is rinsed out of the autoclave with alcohol. After removal of the catalyst, 100 ml of 90 percent strength acetic acid are slowly added to the solution. After addition of water, the reaction product crystallises out. It is dried in vacuo over NaOH. 12.9 g of 1,3-dioxo-6-cyclohexyl-cyclohexane of melting point 137°–140° C. are obtained. After recrystallisation from ethyl acetate, the product has a melting point of 142°–144° C. (literature). Yield: 11.1 g (=55%).

The following substances of the general formula III were prepared analogously to Examples 1 to 4:

| Example | n | $R^1$ | $R^2$ | $R^3$ | $R^4$ | $R^5$ | Salt/base | Melting point (°C.) | $R_F$ value[1] |
|---|---|---|---|---|---|---|---|---|---|
| 5 | 1 | H | CH$_3$ | H | H | H | 2HCl | from 250 (decomposition) | 0.38 |
| 6 | 1 | H | H | H | H | CH$_3$ | ½ oxalate ½H$_2$O | 232–233 (decomposition) | 0.44 |
| 7 | 1 | H | H | CH$_3$ | CH$_3$ | H | 2HCl | 260–265 | 0.39 |
| 8 | 1 | H | n-C$_3$H$_7$ | H | H | H | base | 94–97 | 0.34 |
| 9 | 1 | H | i-C$_3$H$_7$ | H | H | H | oxalate ½H$_2$O | 247–249 (decomposition) | 0.34 |
| 10 | 1 | H | p-CH$_3$O—C$_6$H$_4$— | H | H | H | ½ oxalate H$_2$O | 220–221 (decomposition) | 0.33 |

-continued

| Example | n | $R^1$ | $R^2$ | $R^3$ | $R^4$ | $R^5$ | Salt/base | Melting point (°C.) | $R_F$ value[1] |
|---|---|---|---|---|---|---|---|---|---|
| 11 | 1 | H | $C_6H_5$— | H | H | $CH_3$ | base | 127–129 | 0.53 |
| 12 | 1 | H | $C_6H_5$— | H | $CH_3$ | H | base | 139–141 | 0.37 |
| 13 | 1 | H | —$(CH_2)_5$— | | H | H | base | 157–159 | 0.43 |
| 14 | 1 | H | H | H | $C_6H_5CH_2$— | H | ½ oxalate | 231–233 (decomposition) | 0.34 |
| 15 | 1 | H | H | H | H | H | 2HCl $H_2O$ | 239–240 (decomposition) | 0.31 |
| 16 | 1 | H | H | H | n-$C_6H_{13}$ | H | ½ oxalate $H_2O$ | 198–202 | 0.43 |
| 17 | 1 | H | $C_6H_5$ | H | H | H | base | 133–134 | 0.36 |
| 18 | 1 | $CH_3$ | $CH_3$ | H | $CH_3$ | H | 2HCl | 273–275 | 0.34 |
| 19 | 1 | H | α-naphthyl | H | H | H | base | 173–178 | 0.28 |
| 20 | 1 | H | $C_6H_5$ | H | $C_6H_5$ | H | base | 230–232 | 0.34 |
| 21 | 1 | H | $CH_3$ | $CH_3$ | $CH_3$ | H | 2HCl ½$H_2O$ | 256–257 | |
| 21a | 1 | H | 2-furanyl | H | H | H | base | 118–119 | 0.31 |
| 21b | 1 | H | 2-thienyl | H | H | H | 2HCl | 273–274 | 0.55 |
| 21c | 1 | H | H | —$(CH_2)_4$— ($R^3$ and $R^4$ together) | | H | base | 107–109 | 0.37 |

[1]Conditions corresponding to Example 1

The preparation of the compounds of the formula I according to the invention is illustrated by the following examples:

EXAMPLE 22

1-(4-Amino-6,7-dimethoxyquinazolin-2-yl)-4-(3-oxo-5,5-dimethyl-1-cyclohexen-1-yl)-piperazine dihydrochloride dihydrate A mixture of 4.8 g (0.02 mol) of 2-chloro-4-amino-6,7-dimethoxyquinazoline, 4.6 g (0.022 mol) of (3-oxo-5,5-dimethyl-1-cyclohexen-1-yl)-piperazine and 80 ml of isoamyl alcohol is boiled under reflux for 3 hours, with stirring. During the reaction time, the monohydrochloride precipitates. The mixture is left to stand overnight and the crystals are filtered off with suction. After washing with 40 ml of isoamyl alcohol and twice with in each case 40 ml of absolute acetone and 40 ml of absolute ether and drying, 7.1 g of the hydrochloride of 1-(4-amino-6,7-dimethoxyquinazolin-2-yl)-4-(3-oxo-5,5-dimethyl-1-cyclohexen-1-yl)-piperazine (78% yield) of melting point 267°–268° C. (decomposition) are obtained.

For conversion into the base, the hydrochloride is dissolved in 140 ml of water, and 35 ml of concentrated ammonia solution are added, while cooling with ice. The base which precipitates is extracted twice with 120 ml of chloroform each time and dried with sodium sulphate. After the chloroform solution has been concentrated the residue is recrystallised from about 400 ml of acetonitrile. The base 1-(4-amino-6,7-dimethoxyquinazolin-2-yl)-4-(3-oxo-5,5-dimethyl-1-cyclohexen-1-yl)-piperazine is obtained as a pale yellow-colored substance with a melting point of 186°–188° C.

Conversion of the base into the dihydrochloride dihydrate: 10 g of base are dissolved in 30 ml of methanol and 0.5 ml of concentrated hydrochloric acid are added while cooling with ice. After careful addition of 20 ml of ether, the product crystallises out. 1.0 g of melting point 245°–255° C. (decomposition) are obtained. $R_F$ value: 0.58; eluting agent: $CH_3OH$/ethyl acetate/diethylamine (20:70:5 (by volume)) thin layer chromatography pre-coated plate: silica gel 60 $F_{254}$, with concentration zone, Merck No. 11846

EXAMPLE 22a 1-(4-Amino-6,7-dimethoxyquinazolin-2-yl)-4-(3-oxo-5,5-dimethyl-1-cyclohexen-1-yl)-piperazine A mixture of 2.9 g (0.01 mol) of 2-piperazino-4-amino-6,7-dimethoxyquinazoline, 1.4 g (0.01 mol) of dimedone and 20 ml of toluene is heated at the boiling point under reflux for 4 hours, using a water separator. After cooling the solution, the reaction product precipitates. It is washed with petroleum ether and recrystallised from 220 ml of acetonitrile. 2.6 g of melting point 185°–187° C. are obtained.

$R_F$ value: 0.55 (conditions corresponding to Example 22).

EXAMPLE 23

1-(4-Amino-6,7-dimethoxyquinazolin-2-yl)-4-(3-oxo-5,5-dimethyl-1-cyclohexen-1-yl)-homopiperazine dihydrochloride A mixture of 1.7 g (0.007 mol) of 2-chloro-4-amino-6,7-dimethoxyquinazoline, 2.2 g (0.007 mol) of (3-oxo-5,5-dimethyl-1-cyclohexen-1-yl)-homopiperazine dihydrochloride monohydrate, 3.55 g (0.035 mol) of triethylamine and 30 ml of anhydrous isoamyl alcohol is heated at the boiling point under reflux for 10 hours. After cooling, the triethylamine hydrochloride is filtered off with suction and washed with isoamyl alcohol. The alcohol phases are concentrated at 50° C. in vacuo and the residue which remains is dissolved in 200 ml of chloroform. After washing twice with water, the chloroform solution is dried with sodium sulphate and evaporated to dryness. The residue can be taken up in 20 ml of absolute ethanol. Hydrogen chloride, dissolved in ethyl alcohol, is added to this solution, followed by absolute ether, while cooling with ice, until the onset of turbidity. The 1-(4-amino-6,7-dimethoxyquinazolin-2-yl)-4-(3-oxo-5,5-dimethyl-1-cyclo-hexen-1-yl)-homopiperazine dihydrochloride which precipitates is filtered off with suction and washed with absolute ether. Yield: 2.1 g (60%) of melting point 259°–261° C. (decomposition). A sample recrystallised from ethanol/methanol (2:1) has a melting point of 260°–261° C. (decomposition).

$R_F$ value: 0.47 (conditions corresponding to Example 22).

EXAMPLE 24

1-(4-Amino-6,7-dimethoxyquinazolin-2-yl)-4-[3-oxo-5-(o-chlorophenyl)-1-cyclohexen-1-yl]-piperazine dihydrochloride dihydrate A mixture of 2.4 g (0.01 mol) of 2-chloro-4-amino-6,7-dimethoxyquinazoline, 3.2 g (0.011 mol) of [3-oxo-5-(o-chlorophenyl)-1-cyclohexen-1-yl]-piperazine and 40 ml of isoamyl alcohol is heated at the boiling point under reflux for 3 hours (bath: 150° C.). After cooling, the crystals are filtered off with suction and washed successively with 20 ml of isoamyl alcohol and twice with in each case 20 ml of absolute acetone and anhydrous ethyl. The 1-(4-amino-6,7-dimethoxyquinazoline-2-yl)-4-[3-oxo-5-(o-chlorophenyl)-1-cyclohexen-1-yl]-piperazine hydrochloride, which is dried in vacuo at 40° C., has a melting point of 225°-227° C., with decomposition.

5.0 g (94% yield), yellow crystals.

For conversion into the base, the monohydrochloride is suspended in 20 ml of water, and 15 ml of concentrated ammonia solution are added, with cooling. The base is extracted three times with 200 ml of ethyl acetate each time, the extract is washed twice with 20 ml of water each time and the organic phase is dried with sodium sulphate. After concentration, the base can be recrystallised from isopropanol. For conversion into the dihydrochloride dihydrate, the 1-(4-amino-6,7-dimethoxyquinazoline-2-yl)-4-[3-oxo-5-(o-chlorophenyl)-1-cyclohexen-1-yl]-piperazine thus purified is dissolved in a little methanol, and 0.5 ml, of concentrated hydrochloric acid is added, with cooling. The resulting crystals melt from 200° C. (decomposition).

$R_F$ value: 0.54 (conditions corresponding to Example 22).

EXAMPLE 25

1-(4-Amino-6,7-dimethoxyquinazolin-2-yl)-4-(3-oxo-5-isopropyl-1-cyclohexen-1-yl)-piperazine dihydrochloride dihydrate A mixture of 2.4 g (0.01 mol) of 2-chloro-4-amino-6,7-dimethoxyquinazoline, 2.45 g (0.011 mol) of (3-oxo-5-isopropyl-1-cyclohexen-1-yl)-piperazine and 40 ml of isoamyl alcohol is reacted and worked up as described in Example 24. A monohydrochloride of 1-(4-amino-6,7-dimethoxyouinazoline-2-yl)-4-(3-oxo-5-isopropyl-1-cyclohexen-1-yl)-piperazine is obtained in an amount of 3.1 g (67% yield) with a melting point of 266°-268° C. (decomposition) (yellowish crystals). As described in Example 24, the base is prepared by alkalisation with ammonia. The crude base is extracted twice with 100 ml of chloroform each time and washed twice with 15 ml of water each time. After drying the chloroform phase with sodium sulphate, it is concentrated and the residue which remains is recrystallised with 20 ml of isopropanol. The resulting pure base has a melting point of 269°-271° C. (decomposition) (white crystals). Conversion into the dihydrochloride dihydrate is effected as described in Example 24.

Melting point 240°-243° C. (with decomposition)

$R_F$ value: 0.54 (conditions corresponding to Example 22).

EXAMPLE 26

4-[4-(4-Amino-6,7-dimethoxyquinazoline-2-yl)-1-piperazinyl]-spiro[5,5]undec-3-en-2-one; Spiro-[1-{4-(4-amino-6,7-dimethoxyquinazolino-2-yl)-piperazin-1-yl}-3-oxo-1-cyclohexen]-5,1-cyclohexane dihydrochloride dihydrate ($R^2$ and $R^3$ together=—$(CH_2)_5$—; $R^1$, $R^4$ and $R^5$=H)

A mixture of 4.8 g (0.2 mol) of 2-chloro-4-amino-6,7-dimethoxyquinazoline, 5.45 g (0.022 mol) of [spiro-(3-oxo-1-cyclohexen-1-yl)-5,1'-cyclohexane]-piperazine (4-(1-piperazinyl)-spiro[5,5]undec-3-en-2-one) and 120 ml of isoamyl alcohol is boiled under reflux for 3 hours. After only 5 minutes, a light yellow reaction product precipitates. The mixture is left to stand overnight and the crystals are filtered off with suction. They are washed successively with 40 ml of absolute isoamyl alcohol, 40 ml of absolute acetone and 40 ml of absolute ether. The monohydrochloride is obtained in an amount of 8.1 g (83%) and has a melting point of 277°-278° C. To prepare the base, this amount is dissolved in 150 ml of water, and 40 ml of concentrated ammonia solution are added, while cooling with ice. The base which has precipitated is taken up in 300 ml of chloroform and the mixture is dried with sodium sulphate. After the solvent has been distilled off, a yellow residue remains, which, when recrystallised from acetone, gives spiro-[1-{4-(4-amino-6,7-dimethoxyquinazoline-2-yl)-piperazin-1-yl)-piperazin-1-yl}-3-oxo-1-cyclohexene]-5,1'-cyclohexane . $CH_3COCH_3$ in a yield of 7.8 g. Melting point 163°-172° C. (decomposition). 2.0 g of this product are dissolved in 130 ml of methanol, and 1 ml of concentrated hydrochloric acid followed by 250 ml of ether are added, with cooling. The dihydrochloride dihydrate is obtained in an amount of 2.0 g.

Melting point: 243°-245° C. (decomposition).

$R_F$ value: 0.71 (conditions corresponding to Example 22).

The following substances of the general formula I in which $R^6$ and $R^7$ each denote methoxy groups were prepared analogously to Examples 22 to 26:

| Example | n | $R^1$ | $R^2$ | $R^3$ | $R^4$ | $R^5$ | Salt/Base | Melting point (°C.) | $R_F$ value[1] |
|---|---|---|---|---|---|---|---|---|---|
| 27 | 1 | H | CH₃ | H | H | H | 2HCl 2H₂O | from 200 (decomposition) | 0.5 |
| 28 | 1 | H | H | H | H | CH₃ | 2HCl 2H₂O | 260–264 (decomposition) | 0.55 |
| 29 | 1 | H | H | CH₃ | CH₃ | H | 2HCl 2H₂O | from 200 (decomposition) | 0.55 |
| 30 | 1 | H | n-C₃H₇ | H | H | H | Base | from 180 (decomposition) | 0.53 |
| 31 | 1 | H | H | H | n-C₆H₁₃ | H | HCl | from 270 (decomposition) | 0.6 |
| 32 | 1 | H | p-CH₃O—C₆H₄— | H | H | H | Base | 222–224 | 0.58 |
| 33 | 1 | H | H | H | C₆H₅—CH₂— | H | Base | 148–151 | 0.57 |
| 34 | 1 | H | H | H | H | H | 2HCl 2H₂O | from 180 (decomposition) | 0.47 |
| 35 | 1 | H | H | H | Cyclohexyl | H | Base | 272–275 | 0.59 |
| 36 | 1 | H | C₆H₅ | H | H | H | Base H₂O | 185–197 | 0.58 |
| 37 | 1 | CH₃ | CH₃ | H | CH₃ | H | 2 maleate.H₂O | 185–188 | 0.59 |
| 38 | 1 | H | α-naphthyl | H | H | H | Base H₂O | 175–185 | 0.75 |
| 39 | 1 | H | C₆H₅ | H | H | CH₃ | Base | 275–277 (decomposition) | 0.63 |
| 40 | 1 | H | C₆H₅ | H | CH₃ | H | Base H₂O | 268–269 | 0.54 |
| 41 | 1 | H | C₆H₅ | H | C₆H₅ | H | Base H₂O | >320 (decomposition) | 0.55 |
| 42 | 1 | H | CH₃ | CH₃ | CH₃ | H | Base ½H₂O | 253–255 (decomposition) | 0.6 |
| 43 | 1 | H | 2-furanyl | H | H | H | Base | from 150 (decomposition) | 0.88 |
| 44 | 1 | H | 2-thienyl | H | H | H | Base H₂O | 260–262 | 0.82 |
| 45 | 1 | H | H | —(CH₂)₄— ($R^3$ and $R^4$ together) | | H | Base ½H₂O | 285–286 | 0.6 |

[1]Conditions see Example 22

EXAMPLE 44

Preparation of Tablets

Tablets containing the constituents shown below are prepared by known procedures. These are suitable in a dosage of 1 mg twice daily for treating hypertension and cardiac insufficiency.

| | |
|---|---|
| 1-(4-Amino-6,7-dimethoxyquinazoline-2-yl)-4-(3-oxo-5,5-dimethyl-1-cyclohexen-1-yl)-piperazine dihydrochloride dihydrate | 1 mg |
| lactose | 200 mg |
| maize starch | 25 mg |
| magnesium stearate | 1 mg |

I claim:

1. Substituted 1-(4-amino-6,7-dialkoxyquniazolinyl)-4-cyclohexenyl derivatives of piperazine and homopiperazine, of the formula I

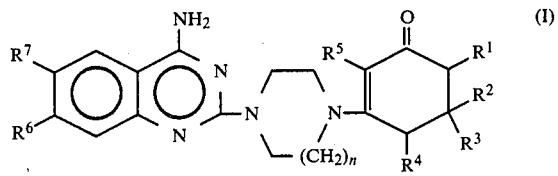

in which $R^1$, $R^2$, $R^3$, $R^4$ and $R^5$, which can be indentical or different, denote hydrogen, straight-chain or branched alkyl with in each case 1 to 6 carbon atoms, carbocyclic aliphatic groups with in each case 5 to 7 carbon atoms, mono- or bi-cyclic carbocyclic aromatic radicals or substituted mono- or bi-cyclic carbocyclic aromatic radicals, which can be monosubstituted or polysubstituted by identical or different substituents selected from the group consisting of halogen, lower alkyl and alkoxy with in each case 1 to 4 carbon atoms in the alkyl part or denote aralkyl radicals in which the alkyl portions is $C_1$-$C_4$-alkyl and the aryl portion is monocyclic carbocylic aryl, furanyl radicals or thienyl radicals, or $R^2$ and $R^3$ together denote the group $-(CH_2)_a-$, wherein a is the number 4 to 5, or $R^3$ and $R^4$ together denote the group $-(CH_2)_b-$ wherein b is the number 3, 4 or 5, $R^6$ and $R^7$, which can be identical or different denote alkoxy groups with 1 to 4 carbon atoms in the alkyl part, which can be straight-chain or branched, and n denotes the number 1 and 2, the tautomeric forms thereof, as well as pharmaceutically acceptable acid addition salts and hydrates thereof.

2. The compound 1-(4-amino-6,7-diemthoxyquinazolin-2-yl)-4-(3-oxo-5,5-dimethyl-1-cyclohexen-1-yl)-piperazine according to claim 1.

3. The compound 1-(4-amino-6,7-dimethoxyquinazolin-2-yl)-4-(3-oxo-5-isopropyl-1-cyclohexen-1-yl)-piperazine according to claim 1.

4. The compound 1-(4-amino-6,7-dimethoxyquinazolin-2-yl)-4-(3-oxo-5-thienyl(2)-1-cyclohexen-1-yl)-piperazine according to claim 1.

5. A pharmaceutical composition containing, as an active ingredient an effective amount of a cardiovascular system regulator of a compound according to claim 1 or a pharmaceutically acceptable acid addition salt thereof in admixture with an inert pharmaceutical carrier.

6. A pharmaceutical composition of claim 5, in oral unit dosage form.

7. A pharmaceutical composition of claim 5 in the form of eye drops or sprays.

8. A pharmaceutical composition containing as an active ingredient an antihypertensively effective amount of a compound according to claim 5 or pharmaceutically acceptazble acid addition salt thereof in admixture with an inert pharmaceutical carrier.

9. A pharmaceutical composition containing as an active ingredient, an effective amount of a cardiac insufficiency treating compound according to claim 5 or pharmaceutically acceptable acid addition salt thereof in admixture with an inert pharmaceutical carrier.

10. A pharmaceutical composition containing as an active ingredient, an effective amount of a glaucomia treating compound according to claim 5 or pharmaceutically acceptable acid addition salt thereof in admixture with an inert pharmaceutical carrier.

* * * * *